(12) United States Patent
Yagita

(10) Patent No.: US 6,504,606 B2
(45) Date of Patent: Jan. 7, 2003

(54) INTEGRATED SOFT BAG INSPECTION SYSTEM

(75) Inventor: Kiyoshi Yagita, Tokyo (JP)

(73) Assignee: Scan Technology Co., Ltd., Tokyo (JP)

( * ) Notice: Subject to any disclaimer, the term of this patent is extended or adjusted under 35 U.S.C. 154(b) by 0 days.

(21) Appl. No.: 09/746,799

(22) Filed: Dec. 22, 2000

(65) Prior Publication Data

US 2002/0039183 A1 Apr. 4, 2002

(30) Foreign Application Priority Data

Oct. 2, 2000 (JP) ........................................ 2000-301865

(51) Int. Cl.⁷ .............................................. G01N 21/00
(52) U.S. Cl. ................................ 356/240.1; 356/239.1; 356/239.4; 356/239.5; 250/223 B; 250/576
(58) Field of Search ......................... 356/240.1, 239.4, 356/239.5, 239.6, 239.1, 239.2, 239.7, 239.8; 250/223 B, 576, 227.1; 73/49.3, 52; 209/602, 522, 524, 525, 526, 529, 530; 602/442; 442/99

(56) References Cited

U.S. PATENT DOCUMENTS

| | | | | |
|---|---|---|---|---|
| 5,388,707 A | * | 2/1995 | Stivison et al. ............. | 209/602 |
| 5,479,969 A | * | 1/1996 | Hardie et al. ................. | 422/99 |
| 5,523,560 A | * | 6/1996 | Manique et al. ......... | 250/223 B |
| 5,844,677 A | * | 12/1998 | Dimmick, Sr. et al. ..... | 356/240 |
| 6,067,155 A | * | 5/2000 | Ringlien ................... | 356/240.1 |
| 6,104,482 A | * | 8/2000 | Brower et al. ........... | 356/239.4 |

FOREIGN PATENT DOCUMENTS

| | | | |
|---|---|---|---|
| JP | 58 117 442 | * | 7/1983 |
| JP | 58 117 443 | * | 7/1983 |
| JP | 409325122 | * | 12/1996 |
| JP | 02000016411 | * | 1/2000 |

* cited by examiner

Primary Examiner—Hoa Q. Pham
Assistant Examiner—Sang H. Nguyen
(74) Attorney, Agent, or Firm—Trask Britt, P.C.

(57) ABSTRACT

An integrated soft bag inspection system overcomes the difficulty of inspection associated with the unstable shape peculiar to soft bags (for example soft bags for intravenous feed use) and makes it possible to carry out inspection of soft bags automatically and with high precision. The system uses a robot having at least a robot hand and has image pickup means for picking up an image of a soft bag and grip position detecting means for detecting a position on a neck part of the soft bag to be gripped by the robot hand on the basis of image information from the image pickup means. A carrying system may be made using a plurality of such robots and carrying control means provided for controlling the robots so that the robot hand of each robot grips the neck part of the soft bag and carries the soft bag to a predetermined inspection position and soft bags arriving from a production line are continuously transferred between adjacent robots and various inspections are carried out on the soft bags successively.

11 Claims, 17 Drawing Sheets

INTEGRATED SOFT BAG INSPECTION SYSTEM

BACKGROUND OF THE INVENTION

1. Technical Field

This invention relates to an inspection system for inspecting a container made of a translucent material which has been filled with a transparent or semi-transparent liquid product on a production line and which will not readily stand on its own in an upright attitude, and particularly to an integrated soft bag inspection system for performing various inspections such as checks for the inclusion of foreign matter and for external defects on a so-called 'soft bag', a flat, pliant container filled with an intravenous feed solution or the like.

2. Prior Art

As the applicable food sanitary laws are based on HACCP and the PL (product liability) regulations are enforced, it will be obligatory to avoid any undesired incident, such as microbial contamination or entrance of impurities, which may occur in all steps of food quality control from the production and process of food and medicine products to storage, shipment, and consumption of the products and to increase the cleanliness and the safety of such products.

HACCP stands for hazard analysis of critical control points which has been developed in U.S.A. and is known throughout the world as one of the best sanitary control system methods. The HACCP is intended for evaluating the safety of products in all manufacturing processes as compared with conventional sanitary control methods where the final products are a subject to be inspected the HACCP particularly focuses on the preventive quality control in each process and consists mainly of two major sections: hazard analysis and critical control points. Any possibility of hazardous incidents such as microbial contamination which may occur in each step of the manufacturing and processing of foods and the storage and shipment of products before the end consumers is reviewed and analyzed through determining the critical control points for preventive actions and the control standards and constantly monitoring and checking the records of control whether or not the requirements are fulfilled within allowance. Also, other hazardous items are controlled by the pre-requisite program to prevent any adulteration in the process and to improve the safety quality of products.

In manufacturing and processing plants for liquid products (e.g. beverages and liquid medicines), heating and pasteurization processes are used for preventing microbial contamination in the production line and removal of impurities with cyclone separators or the like is implemented for adulteration. After a container such as a can or a bottle is filled, a final inspection is carried out utilizing light transmission or reflection. For example, when a transparent container filled with a liquid such as a medicine or a drink is the product to be inspected, an image of the container is picked up with a CCD camera and digitized image data is processed by an image-processor to check for the presence of foreign matter included in the liquid inside the container and for flaws in the container and so on, and on this basis a determination of whether the final product is good or defective is made automatically.

Containers filled with a liquid product like this are normally cylindrical or prismatic like PET bottles and beer bottles. A container of this kind can stand up on its own, and, because it is made of a relatively hard material, will not deform when laid on its side, stood upside-down or tilted. Nor will such a container deform when gripped from both sides and carried or rotated by gripping belts. Because of this it is relatively easy to bring the container to a desired attitude using certain carrying mechanisms and inspection mechanisms, and consequently the detection of included foreign matter and the detection of flaws in the container can be carried out automatically using an image-processing device.

However, in the case of a so-called 'soft bag', a flat, pliant container filled with an intravenous feed solution or the like, because the shape readily deforms and the surface easily suffers damage, with related art inspection equipment inspection has not been possible, and it has not been possible to adapt foreign matter inspection systems designed for inspecting bottles and the like to be used for inspecting soft bags. Consequently, it has been the situation that inspections carried out after a soft bag is filled with a liquid product are carried out by hand, visually. For example, generally an inspector has held a soft bag arriving on a belt conveyor or the like in the hand, held the face of the soft bag up to an electric lamp or a fluorescent light, and checked for included foreign matter and flaws in the bag visually. And because small foreign bodies and transparent container fragments and the like are difficult to detect with the human eye, there has been a danger of foreign bodies going undiscovered. Also, with automatic production on a production line this inspection step has constituted a bottleneck, and for mass production a large number of people have been needed for the inspection stage.

SUMMARY OF THE INVENTION

It is therefore an object of the present invention to overcome the difficulty of inspection associated with the unstable shape peculiar to soft bags, and provide an integrated soft bag inspection system which makes it possible to carry out inspection of soft bags automatically and with high precision.

The present invention relates to an integrated soft bag inspection system for inspecting a soft bag having been filled with a liquid on a production line using a robot having at least a robot hand, and to achieve the above-mentioned object and other objects the invention provides image pickup means for picking up an image of the soft bag and grip position detecting means for detecting a position on a neck part of the soft bag to be gripped by the robot hand on the basis of image information from the image pickup means.

Preferably, there are further provided a table made from a transparent material on which the soft bag is placed lying on its side and a flat light for shining a substantially uniform light toward the underside of the table, and the grip position detecting means detects the position to be gripped on the neck part on the basis of an image of the soft bag picked up by the image pickup means from above the table: the table is made of a hard glass filter comprising an optical filter for preventing diffused reflection; and a carrying system is made up of a plurality of robots and there are provided carrying control means for controlling the robots so that the robot hand of each robot grips the neck part of the soft bag and carries the soft bag to a predetermined inspection position and the soft bag is transferred between adjacent robots, and various inspections are carried out on the soft bag successively.

And preferably, the soft bag is a bag for intravenous feed use filled with an intravenous feed solution and the inspections include a foreign matter inspection and at least one inspection from among the group consisting of a seal peeling inspection of a top face part of the soft bag, a dirt inspection of a port part, a shape defect inspection, a print-blurring inspection and inspection for a different sort of product; a plurality of robots are disposed on a soft bag inspection stage in two lines facing each other and soft bags arriving in a single line from a production line are carried distributed between the robots of the two lines; and, of soft bags arriving continuously in a single line from the production line, soft bags in odd positions in the line are carried by one of the lines of robots and soft bags in even positions are carried by the other line of robots.

And preferably, for inspecting a soft bag having been filled with a liquid on a production line, there are provided image pickup means for picking up an image of the soft bag and laser light radiating means for radiating laser beams in the form of a mesh over an entire face of the soft bag, and whether the soft bag is good or defective is checked on the basis of image information from the image pickup means by detecting disruption of an image of the mesh form. Also, preferably an optical filter is provided between the soft bag and the image pickup means.

The invention also provides an integrated soft bag inspection system having at least two inspection steps for inspecting a soft bag having been filled with a liquid on a production line, wherein a step of printing information which must be printed on the soft bag in the production line is provided before a final step and thus the printed information is printed and inspected within the inspection process.

The invention also provides an integrated soft bag inspection system for inspecting in real time every one of soft bags arriving continuously from a production line having been filled with a liquid on the production line, using robots each having at least a robot hand as carrying means for carrying the soft bags, comprising: image pickup means for picking up an image of a soft bag; grip position detecting means for detecting a position on a neck part of the soft bag to be gripped by the robot hand of a robot on the basis of image information from the image pickup means; first inspection means for, on the basis of image information from the image pickup means picked up with the soft bag gripped by the neck part and held upright by a robot hand, performing a seal peeling inspection of a top face part of the soft bag and a dirt inspection of a port part; second inspection means for, on the basis of image information from the image pickup means picked up with laser beams in the form of a mesh being radiated over an entire face of the soft bag, inspecting for shape defects including sealing defects of the soft bag proper by detecting disruption of the mesh-form image; third inspection means for, on the basis of image information from the image pickup means picked up with the soft bag placed lying on its side on a table made from a transparent material, inspecting for foreign matter including foreign matter included in the soft bag; fourth inspection means for, on the basis of image information from the image pickup means picked up with the soft bag placed lying on its side on a table made from a transparent material, inspecting for blurring of printed information pre-printed on the soft bag and inspecting for whether a different sort of bag is included; printing means for printing on the soft bag while the soft bag is being carried by the robot in a vertical attitude information which must be printed on the soft bag on the production line; and fifth inspection means for inspecting the printed information printed by the printing means.

Preferably, the third inspection means performs the inspection for foreign matter on the basis of image information from the image pickup means picked up with the soft bag placed on the table so that a printed face of the soft bag is uppermost and with the flat light brought close to or into contact with a flat face of the soft bag; and the fourth inspection means performs the inspection for blurring of the printed information and for whether a different sort of bag is included on the basis of image information from the image pickup means picked up with the soft bag placed on the table so that a printed face of the soft bag is lowermost and with the flat light brought close to or into contact with a flat face of the soft bag.

DESCRIPTION OF PREFERRED EMBODIMENTS

A product to be inspected in this invention is a container which is made of a translucent material and has been filled with a transparent or semi-transparent liquid product on a production line and which will not readily stand on its own in an upright attitude. In particular, the invention can be ideally applied as an integrated soft bag inspection system for performing various inspections such as checks for foreign matter defects and appearance defects on a so-called 'soft bag', a flat, pliant container filled with a solution such as an intravenous feed solution. In the following, a preferred embodiment of the invention will be described in detail using as an example the case of inspecting a soft bag filled with an intravenous feed solution. Types of soft bag for intravenous feed use include soft bags for general use and soft bags for kit use. There are four sizes of soft bag for general use: 300 ml, 200 ml, 100 ml and 50 ml, and two sizes of soft bag for kit use: 200 ml and 100 ml, and any of these soft bags can be inspected by the system described here.

Figure 1:
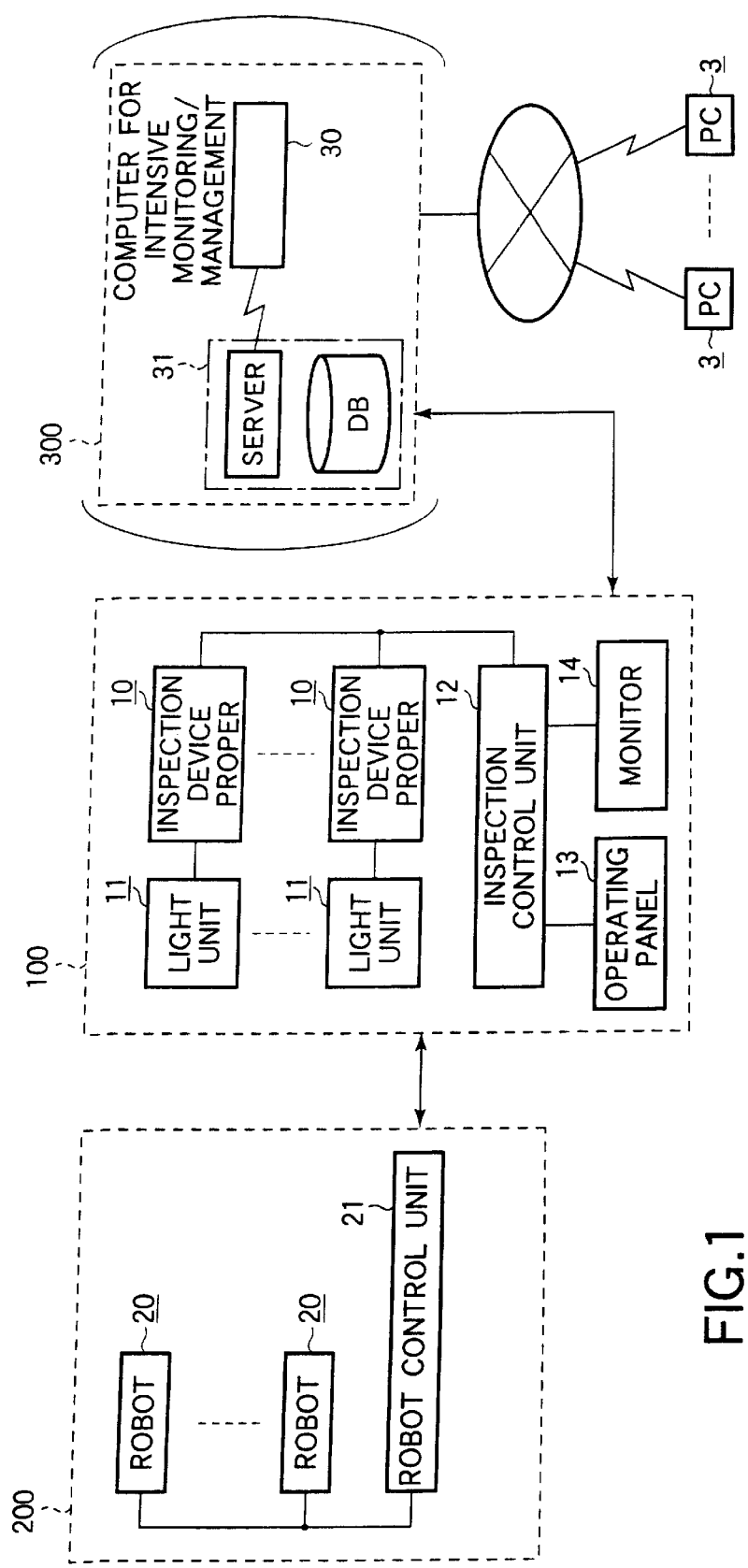
FIG. 1 is a block diagram showing an example of the overall construction of an integrated soft bag inspection system according to the invention.

FIG. 1 is a block diagram of the overall constitution of an integrated soft bag inspection system according to the invention. The system is made up of two main blocks: an image-processing inspection system 100 and a robot carrier system 200. As shown in FIG. 1, the image-processing inspection system 100 is made up of inspection devices 10 proper (hereinafter, 'inspection devices') 10, light units 11, an inspection control unit 12, an operating panel 13 having a touch panel, and a monitor 14. The inspection devices 10 and the inspection control unit 12 are all housed in a single case (control panel).

In FIG. 1 there is additionally provided an FA server system 300, and by using this FA server system 300 it is possible to upload all inspection data such as good/defective information and rejected product data to a database server 31 in real time. Also, monitoring and remote control from communication terminals 3 such as personal computers become possible, and optimization of various settings of the integrated soft bag inspection system can be carried out easily. Furthermore, at the side of connected to a computer for intensive monitoring/management or communication terminal 3 through a network such as a LAN or the internet it becomes possible to execute analysis of various inspection conditions and clarification of causes of foreign matter inclusion without delay.

In inspection in the image-processing inspection system 100, various functions such as automatic correction of positional deviation of inputted images and free adjustment of precision to match conditions on the line are executed mainly by hardware processing. All this processing is carried out in real time, and highly precise inspection of all units of product on a high-speed mass production line such as has hitherto not been possible is realized. And in inspection for foreign matter, a multiple analog differential slice method and a difference method based on multiple scans are employed to overcome the unstable shape peculiar to the soft bag and make possible the automatic detection of foreign matter in a liquid that has been a theme for many years.

Figure 2:
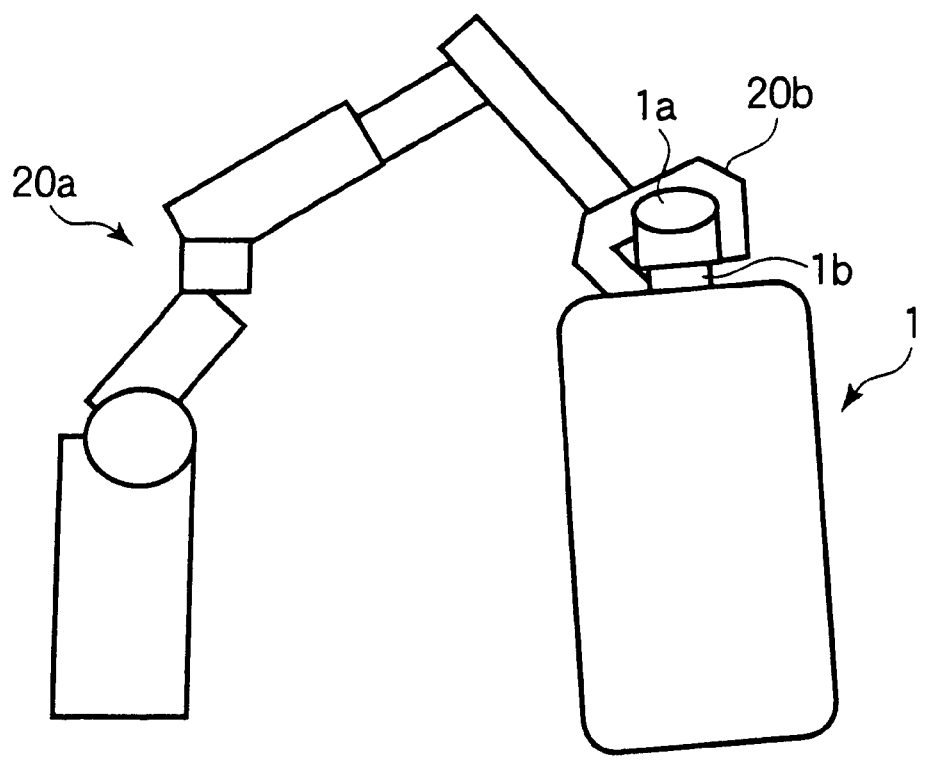
FIG. 2 is a schematic view showing an example of a robot according to the invention and a state of gripping a product to be inspected.

The robot carrier system 200 is made up of carrier robots 20 for gripping products to be inspected and carrying them to inspection stations and a robot control unit 21 for controlling these robots. As shown in FIG. 2, each of these robots 20 used as carrying means has at least an arm 20a which can bend and turn at joints thereof and a gripping part 20b (hereinafter, robot hand) for gripping a product to be inspected 1 (in this example, a soft bag), and can grip a neck part 1b of a soft bag 1 with a top face part 1a uppermost by means of the robot hand 20b and carry the soft bag 1 to a specified inspection position of a respective inspection device by movement control using rotation and bending of the arm 20a. And because the robot 20 carries the work by the neck part like this, operations such as bringing the work to the vertical and tilting it can be carried out without damaging the bag.

Figure 3:
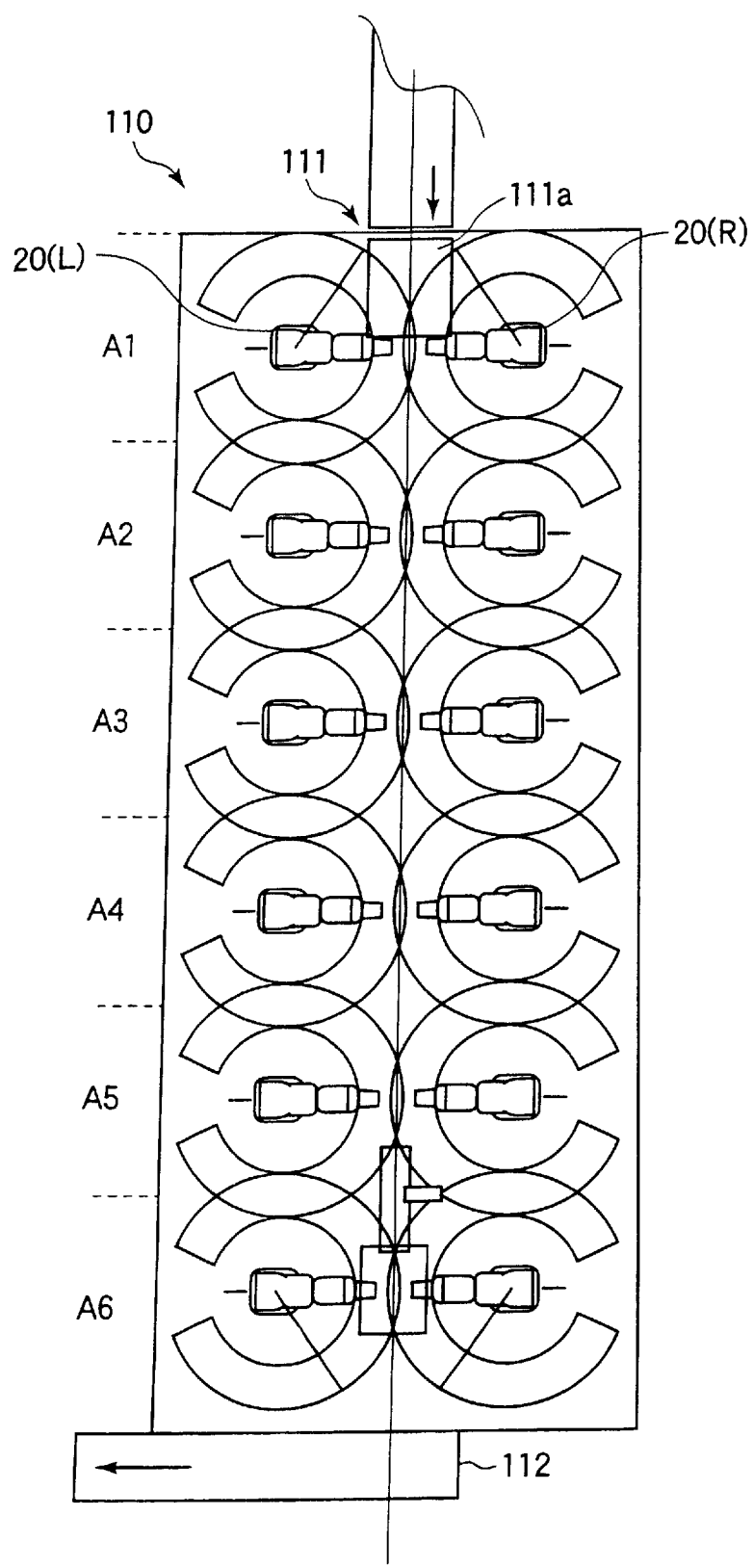
FIG. 3 is a plan view showing an example of an arrangement of robots constituting a robot carrying system according to the invention.

FIG. 3 shows an example of an arrangement of the robots 20 of the robot carrier system 200. A carrying procedure using the robots will now be described with reference to this figure.

The robots 20 used as carrying means are installed on an inspection stage 110, where various checks are carried out. In this example, a robot installation area on the inspection stage 110 is divided into six areas A1 through A6, and two robots 20 are installed facing each other in each of the areas A1 through A6. In the example of FIG. 3 the carrying system is made up using 6 robots in 2 lines, or a total of 12 robots, and soft bags arriving in a singe line from the production line are divided between the robots 20(L) and 20(R) of these two lines. In this preferred embodiment, of the soft bags arriving in a single line from the production line, soft bags in odd positions in the line are carried by one of the lines of robots 20 and soft bags in even positions are carried by the other line of robots 20. By employing this kind of carrying sequence, time loss arising after a soft bag is carried to a destination position by a robot arm turning, that is, time lost while the arm returns to its original position, can be covered by a robot in the other line, and rapid carrying of the soft bags becomes possible.

Here, a specific example of a carrying procedure will be described. In FIG. 3, a soft bag arriving from the production line on carrying means such as a belt conveyor is deposited on a table for position detection 111a mounted on an entrance part 111 of the inspection stage 110, and a position at which a robot 20 is to grip the soft bag 1 is determined in an area A1 step. Then, while this soft bag is gripped and transferred to an adjacent robot 20 by the first robot 20 in for example the right line, the first robot 20 in the left line grips and processes the next soft bag, and in this way soft bags 1 arriving continuously at predetermined intervals are gripped and carried to the adjacent area A2 alternately by robots of the left and right lines. Between adjacent areas, the two robots 20 adjacent in the line respectively grip an upper side portion and a lower side portion of the neck part of the soft bag, and the soft bag is transferred while in mid-air.

The carrying rate of the robots 20 on the inspection stage 110 is the same as the rate at which the soft bags arrive from the production line, and for example is a carrying rate of about 1 soft bag per second (3200/hr). In the image-processing inspection system 100, all of the soft bags arriving at this rate are inspected.

Figure 4:
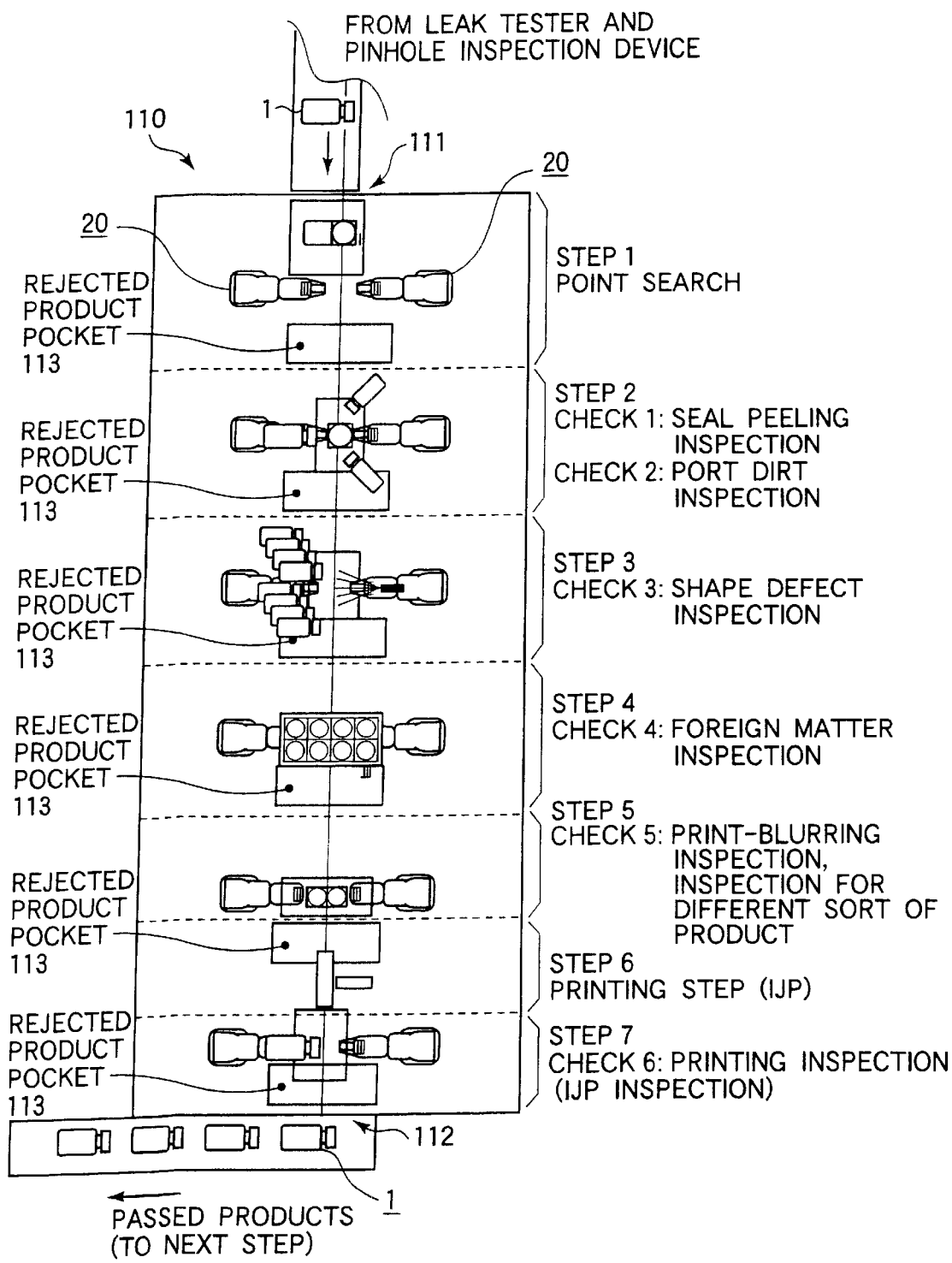
FIG. 4 is a plan view showing an example of an arrangement of robots and inspection equipment installed on an inspection stage according to the invention.

FIG. 4 shows in plan view an example of an arrangement of the inspection equipment and robots disposed on the inspection stage 110. In this preferred embodiment, taking into account theoretical ease of image-processing inspection and motional advantages to robot handling, the inspection items are divided into six steps. In the example shown in FIG. 4, the inspection items are divided into steps 1 through step 5 and step 7; a printing step 6 is provided before the final step, step 7 (in this example, between the inspection steps step 5 and step 7), and printed information which must be printed on the soft bags in the production line, such as a date of manufacture, is printed during the inspection process. A detailed description of the steps 1 through 7 will be given later. Here, with reference to the layout of the inspection stage 110 shown in FIG. 4, an outline of inspection flow in the integrated soft bag inspection system and the inspection items of the different steps will be discussed.

Soft bags 1 filled with intravenous feed solution on the production line arrive continuously at the entrance part 111 of the inspection stage 110, lying on their sides with their neck parts pointing in the same direction. After the position at which a soft bag is to be gripped is detected in step 1, the robots 20 are controlled to carry the soft bag 1 successively to specified positions of steps 2 through 7, and the various inspections (and printing in step 6) are carried out. And if it has passed all of the inspections, the soft bag 1 is carried out through an exit part 112 and transferred to a subsequent production step. The predetermined areas for the inspection steps divided up in correspondence with inspection items are each provided with a rejected product pocket 113, and any soft bag 1 determined to have failed an inspection is discarded through the respective rejected product pocket 113. In this way, products rejected at the stages of different steps are sorted automatically. Passed products only are carried out through the exit part 112, and are transferred by carrying means such as a belt conveyor to the next production step.

The different steps in the inspection stage 110 and the inspection items will now be discussed.

Step 1 is a step of obtaining a target point for when the robot hand grips the soft bag, and this target point is obtained using one inspection device for target point searching. Step 2 is a step of carrying out a check 1 with 'seal peeling' as the inspection item and a check 2 with 'port dirt' as the inspection item, and these checks 1 and 2 are carried out in parallel using one inspection device for detecting seal peeling and three inspection devices for detecting port dirt. Step 3 is a step of carrying out a check 3 with 'defective shape', such as a sealing defect of the seal part of the soft bag proper (a seal affixed to the top face part), as the inspection item, and in this step eight inspection devices for detecting shape defects are used to inspect eight respective parts of an inspection region. Step 4 is a step of carrying out a check 4 with 'foreign matter check' as the inspection item, and in this step eight inspection devices for detecting foreign matter are used to inspect eight respective parts of an inspection region. The reason for dividing up the inspection region and inspecting it using multiple inspection devices is to improve inspection precision and to increase inspection speed.

Step 5 is a step of carrying out a check 5 with 'blurred printing' and 'a different sort of product (inclusion of wrong product)' as inspection items, and in this step two inspection devices are used to inspect two respective parts of an inspection region. In this step 5, the subject of the inspection is printing printed on the soft bag in advance. Printed information that must be printed on the production line (information such as the date of manufacture and a serial number) is inspected in step 7. Step 6 is a step of printing this printed information in a predetermined position on the soft bag, and in this example printing is carried out using an IJP (Ink Jet Printer) while the soft bag is being carried. Whereas in related art this printed information such as the date of manufacture has been printed before a heating step and the heating has caused the printing to become thin, in this invention, by printing being carried out during the inspection process, this kind of problem is eliminated. Step 7 is a step of carrying out a check 6 with 'printing inspection' of the information printed in step 6 as the inspection item, and in this step the inspection is carried out using one inspection device (an inspection device for detecting blurred printing and a different sort of product).

Next, examples of arrangements of light units used in the different steps and the constructions of the light units will be described, with reference to the layout views of FIG. 5 through 10. An optical filter used in the light units 11 will be discussed later in a detailed description of the processing of each step.

Figure 5:
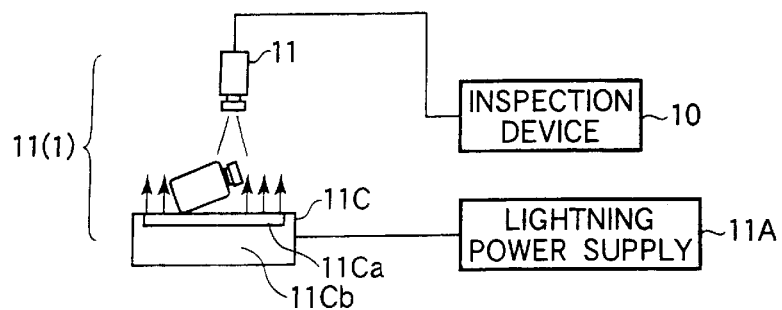
FIG. 5 is a schematic view showing an example of a light unit arrangement for a first step according to the invention.

FIG. 5 shows an example of a light unit arrangement for step 1. Here, a light unit 11(1) is made up of a lamp house 11C, having a table 11C$a$ made of a transparent material on which a soft bag 1 is placed on its side (lying with its flat faces horizontal) as a product to be inspected and uniform illumination means 11C$b$ (hereinafter, 'flat light') for shining a substantially uniform light vertically through the table from below, and a camera 11, mounted above the lamp house 11C, for picking up an image of the neck part of the soft bag 1. In this preferred embodiment, a glass plate is used as the transparent table 11C$a$; a flat light having an annular light-emitting part of a size corresponding to the light-receiving part of the camera is used as the uniform illumination means 11C$b$; and a CCD camera is used as the image pickup means (camera) 11. Also, a lighting power source 11A such that the strength of the light can be controlled by commands from outside is used. Hereinafter, parts the same as parts described here have been given the same reference numerals and will not be described again. And although the construction of the image processing hardware differs among the inspection devices, for convenience they have all been given the same reference numeral.

Figure 6:
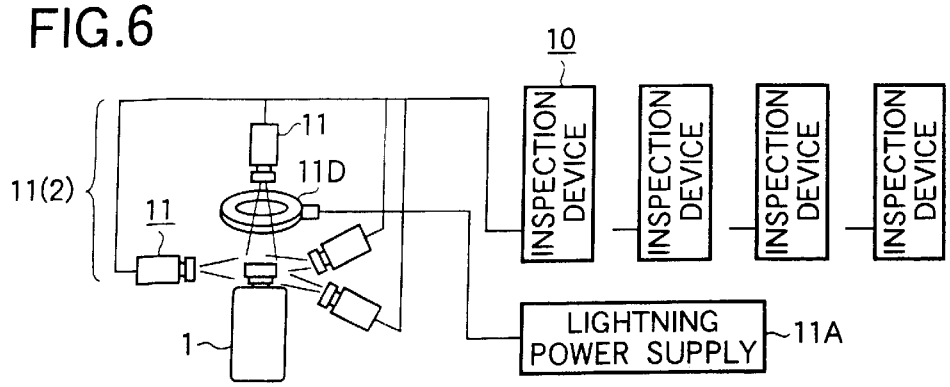
FIG. 6 is a schematic view showing an example of a light unit arrangement for a second step according to the invention.

FIG. 6 shows an example of a light unit arrangement for step 2. Here, a light unit 11(2) is made up of a ring light 11D for shining an annular or cylindrical light beam onto the top face part of a soft bag 1 in an upright attitude; one camera 11, mounted above the soft bag 1, for picking up an image of the top face part of the soft bag 1; and three cameras 11, mounted around the port of the soft bag 1, for picking up an image of the entire circumference of the port. Each of the cameras 11 is connected to its own inspection device 10.

Figure 7:
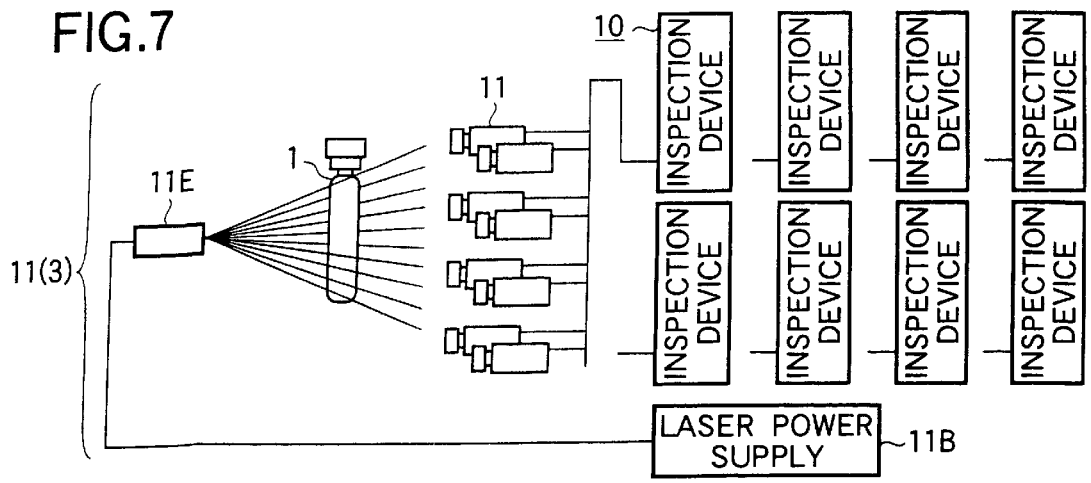
FIG. 7 is a schematic view showing an example of a light unit arrangement for a third step according to the invention.

FIG. 7 shows an example of a light unit arrangement for step 3. Here, a light unit 11(3) is made up of a laser light irradiation device 11E for shining multiple laser beams in the form of a matrix (grid-form laser beams) toward a flat face (hereinafter, 'side face') of a soft bag 1 in an upright attitude; a power source 11B of the laser light irradiation device 11E; and eight cameras 11 for picking up images of respective regions of the other side face of the soft bag 1.

Figure 8:
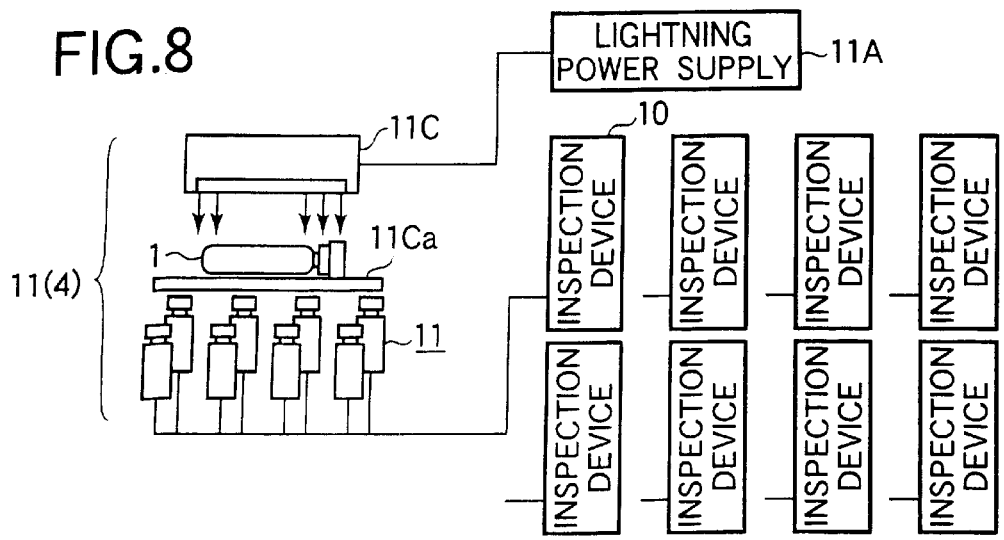
FIG. 8 is a schematic view showing an example of a light unit arrangement for a fourth step according to the invention.

FIG. 8 shows an example of a light unit arrangement for step 4. Here, a light unit 11(4) is made up of a table 11C$a$ made of a transparent material on which a soft bag 1 is placed on its side; a lamp house 11C for shining a substantially uniform light vertically through the table 11C$a$ from above; and eight cameras 11, mounted below the lamp house 11C, for picking up images of eight respective regions of the side face of the soft bag 1.

Figure 9:
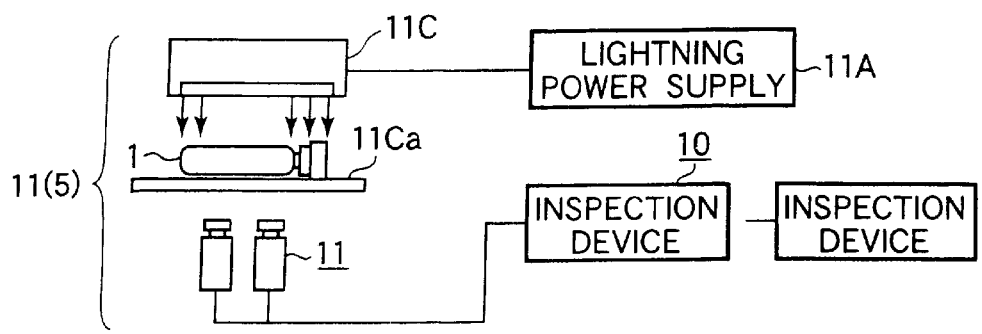
FIG. 9 is a schematic view showing an example of a light unit arrangement for a fifth step according to the invention.

FIG. 9 shows an example of a light unit arrangement for step 5. Here, a light unit 11(5) is made up of a table 11C$a$ made of a transparent material on which a soft bag 1 is placed on its side; a lamp house 11C for shining a substantially uniform light vertically through the table 11C$a$ from above; and two cameras 11 for picking up images of two respective regions of the side face of the soft bag 1.

Figure 10:
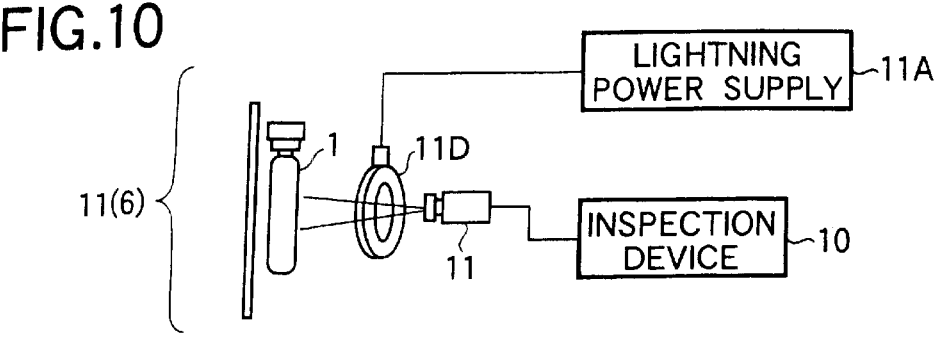
FIG. 10 is a schematic view showing an example of a light unit arrangement for a seventh step according to the invention.

FIG. 10 shows an example of a light unit arrangement for step 7. Here, a light unit 11(6) is made up of a ring light 11D for illuminating a side face of a soft bag 1 in an upright attitude and one camera 11 for picking up an image of a printed region, printed in step 6, of the side face of the soft bag 1.

The processing of the different steps in an integrated soft bag inspection system according to the invention constructed as described above, including inspection principles, will now be explained. The checks and printing of steps 2 through 6 are carried out without the carrying system being stopped.

[Step 1]

Because when the bag part, filled with a solution, of a soft bag is gripped by a robot hand there is a possibility of it being damaged, in this system, each soft bag is gripped and carried by its neck part. Since the neck part of a soft bag for intravenous feed use does not have a uniform cylindrical shape but rather is formed with steps, and the soft bags are to be transferred between adjacent robots, it is important for the robot hand to grip the neck part in the correct position. Accordingly, in step 1, to enable the robot hand to automatically recognize a gripping position on the soft bag, image-processing is carried out on the neck part of the soft bag to obtain a target point.

Figure 11:
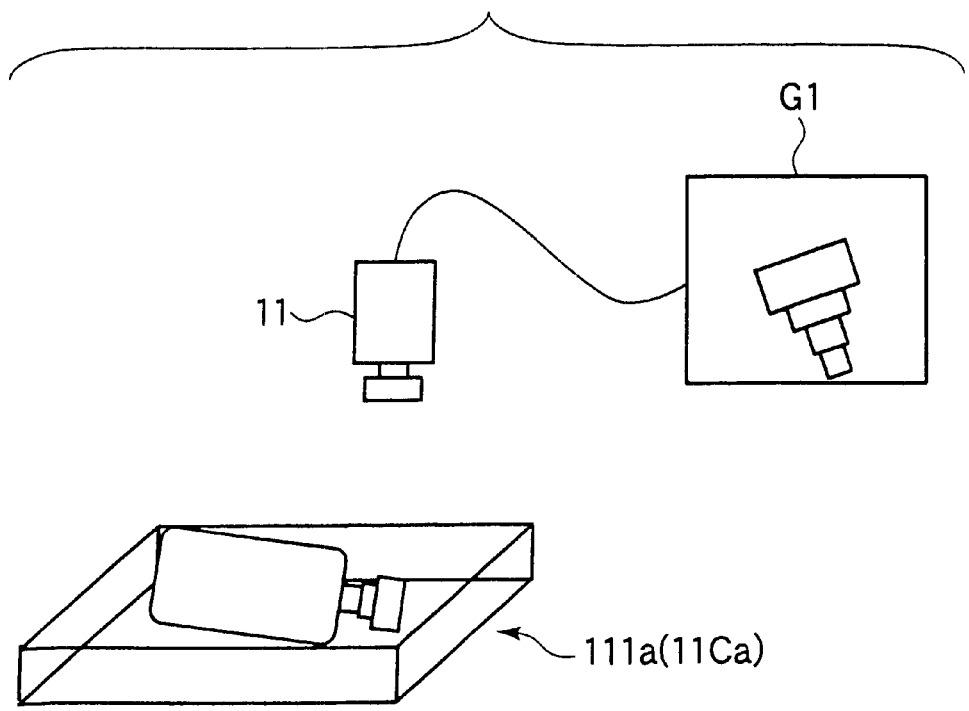
FIG. 11 is a first schematic view illustrating processing in the first step.

This processing for obtaining a target point will now be described with reference to FIG. 11. A soft bag 1 arriving from the production line is deposited on the table for position detection 111*a* (the transparent table 11C*a* of the lamp house 11C) provided at the entrance of the inspection stage 110 from the end portion of the production line. The transparent table 11C*a* of the lamp house 11C is formed in a stepped shape with three steps to correspond with different types of soft bag, for example small, medium and large sizes, and the soft bag 1 is roughly positioned by these steps when it is carried in from the production line upstream and deposited on its side on the transparent table 11C*a*. Light is shone by the flat light 11C*b* from below the soft bag 1 on the transparent table, an image of the neck part of the soft bag 1 is picked up by the camera 11 mounted thereabove, and this image G1 is taken in by the inspection device 10 for target point searching.

Figure 12:
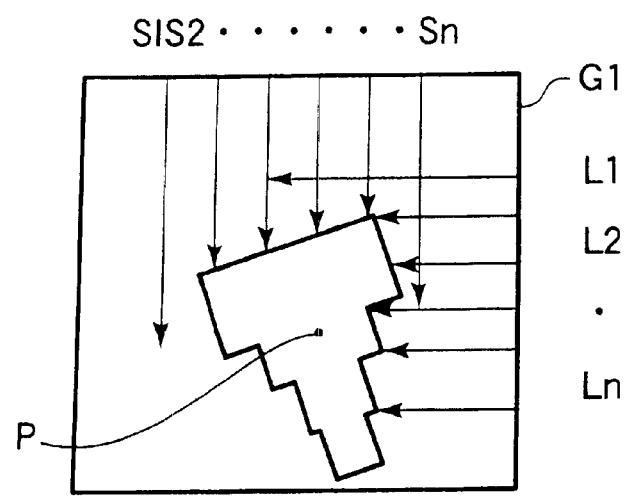
FIG. 12 is a second schematic view illustrating processing in the first step.

Then, as shown in FIG. 12, a signal of vertical sampling lines S1 through Sn and a signal of horizontal sampling lines L1 through Ln are taken in; an image-processing part of the inspection device performs a search on the neck part image G1 from the vertical and cross directions (the vertical line direction and the horizontal line direction) to detect intersection points (edges) of the neck part; and on the basis of this neck part detection information the position of a target point P on the neck part at which the robot hand should grip is obtained. This position information is sent from the inspection device for target point searching 10 via the robot control unit 21 to the respective robot 20 mounted in the area of step 1 and is also sent to the other robots 20 (the robots in the same line), and is used to specify the positions at which the soft bag 1 is to be gripped. In this step 1, when an abnormality of the shape of the neck is detected, the soft bag is discarded by being dropped into the respective rejected product pocket 113.

[Step 2]

Figure 13:
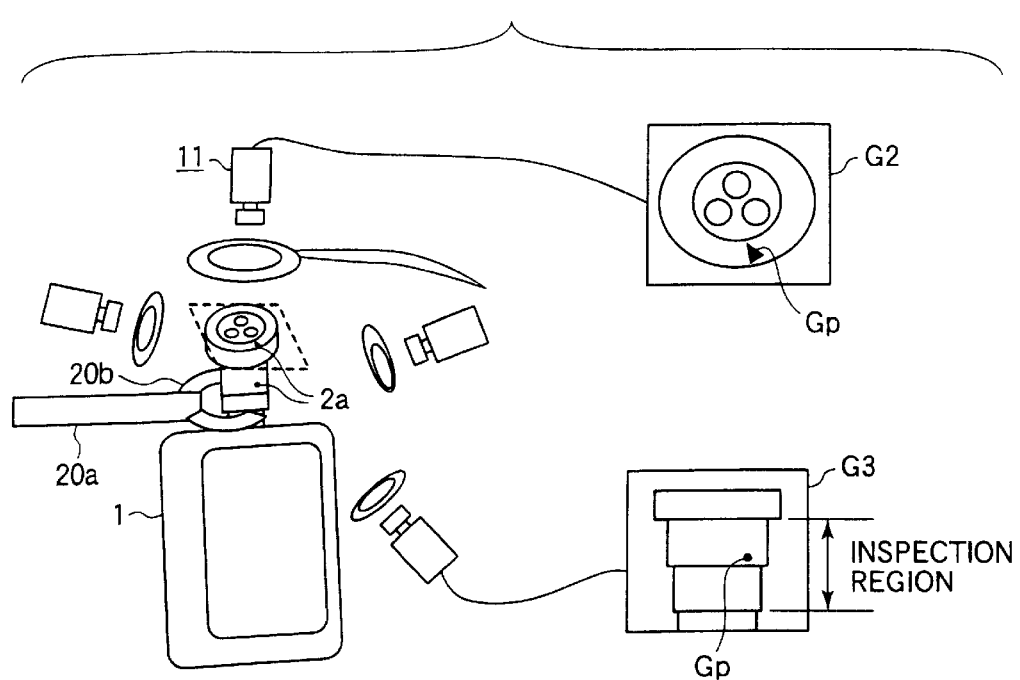
FIG. 13 is a schematic view illustrating processing in the second step.

In step 2, seal peeling defects are detected with a camera from above the top face, and port dirt defects are detected with cameras from the side. This detection processing will now be described with reference to FIG. 13. A soft bag 1 is carried to a specified inspection position for step 2 by a robot 20 disposed in the area for step 1. In step 2, the neck part of the soft bag 1 is gripped by the respective robot 20 of step 2 and turned to the upright and carried in a hanging state while an image G2 of the top face of the bag is taken by the top face camera 11 and simultaneously an image G3 of the entire circumference of the port part is taken by the three side cameras (the image G3 in FIG. 13 is an example of an image from one camera). Since a defective part 2*a* of the port part shown in FIG. 13 appears as a pixel Gp, the inspection device for detecting seal peeling and the inspection device s for detecting port dirt respectively detect seal peeling defects and port dirt defects by counting these pixels. When a defect is detected the soft bag is discarded by being dropped into the respective rejected product pocket 113, while soft bags passing the inspection are carried to the specified inspection position of the following step 3.

[Step 3]

Figure 14:
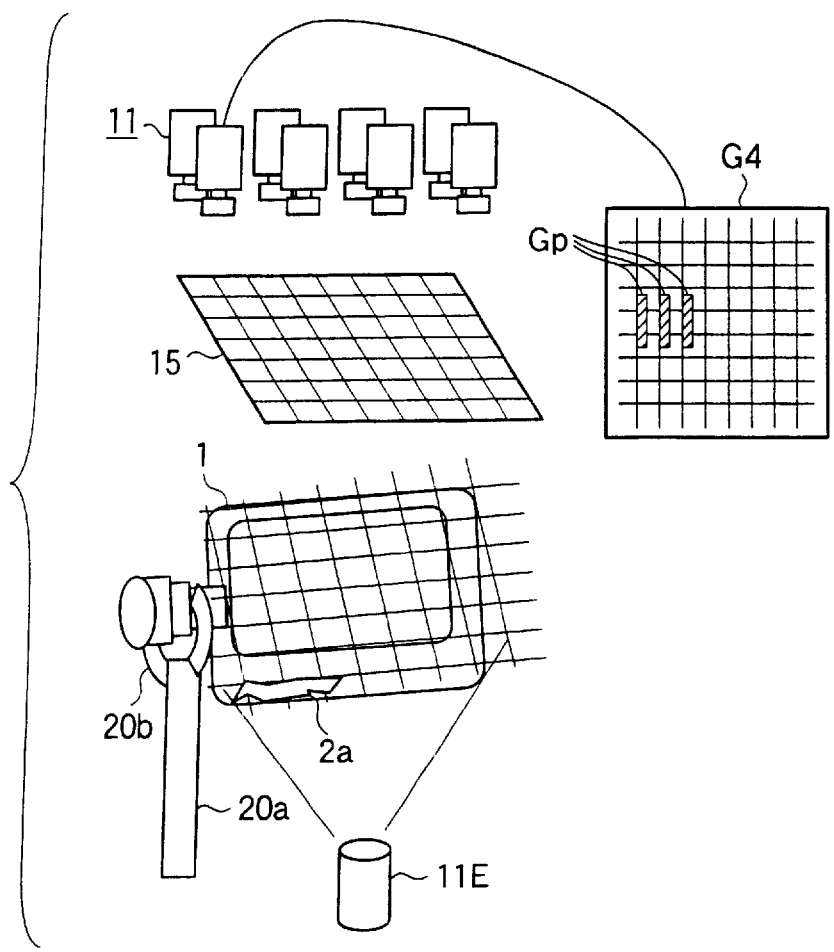
FIG. 14 is a first schematic view illustrating processing in the third step.
Figure 15:
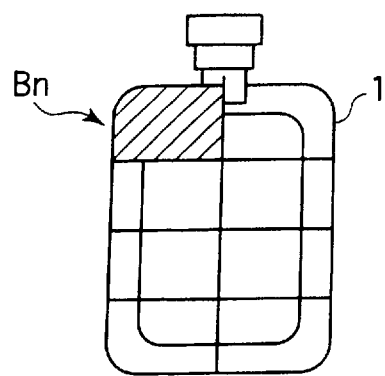
FIG. 15 is a second schematic view illustrating processing in the third step.

In step 3, sealing defects of the seal part of the soft bag proper are detected with side cameras. This detection processing will now be described with reference to FIG. 14. In step 3, while the respective robot 20 of step 3 carries the soft bag 1 in an upright attitude, laser beams in the form of a grid (a mesh) are shone over the entire region of the side of the soft bag 1 by the laser light irradiation device 11E, and images of respective parts of the side face of the soft bag 1 are pickup up the eight cameras 11 through an optical filter 15 provided between the soft bag 1 and the cameras 11. In this construction, when laser light strikes a defective part 2*a* it refracts, and consequently, like the parts shown with the symbol Gp in the image G4 of FIG. 14, the squares in the image are disrupted. The inspection devices for detecting shape defects detect this disruption from the image information of the grid of laser beams and determine this disruption to be a defect. When a defect is detected the soft bag is discarded by being dropped into the respective rejected product pocket 113, while soft bags passing the inspection are carried to the specified inspection position of the following step 4. As the optical filter 15, which is for preventing diffused reflections caused by twisting of the bag or the like, a white non-transparent filter is used. And because the product being inspected may be a soft bag of any size from 50 ml to 300 ml, the field of view is divided into eight on the basis of a calculated value of a necessary resolution and, as shown in FIG. 15, the inspection is carried out with eight cameras each given a field of view Bn (n=1 to 8). This division inspection method is also the same in the other steps in which multiple cameras are used to pick up images of respective divisions of the overall region being inspected.

[Step 4]

Figure 16:
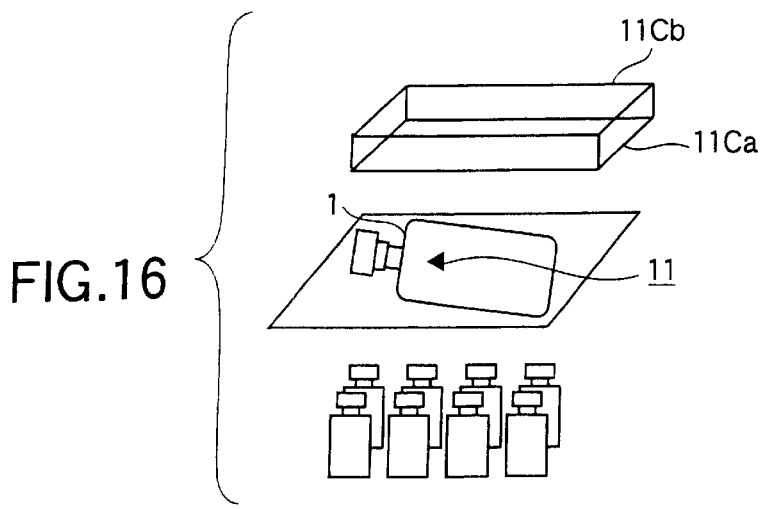
FIG. 16 is a first schematic view illustrating processing in the fourth step.

In step 4, the soft bag lying down is shot by cameras from below to detect foreign matter in the liquid and foreign matter included in the bag and the like. This detection processing will be described with reference to FIG. 16. In step 4, the respective robot 20 of step 4 places the soft bag 1 on the inspection table 11C*a* so that a flat face of the soft bag 1 is positioned on the upper face of the table 11C*a* and the printed side is up (facing the flat light 11C*b*), and the flat light 11C*b* is brought close to or into contact with the flat side of the soft bag 1 (and thus close to the face of the glass plate 11C*a*). With the soft bag 1 in this state, the flat light 11C*b* is used to shine a uniform light toward the glass plate 11C*a* from above and the eight cameras 11 mounted below the table 11C*a* pick up the light transmitted through the soft bag 1 and the table 11C*a* and take an image of the entire flat face of the soft bag 1, and foreign matter is detected by the following image-processing.

Figure 17:
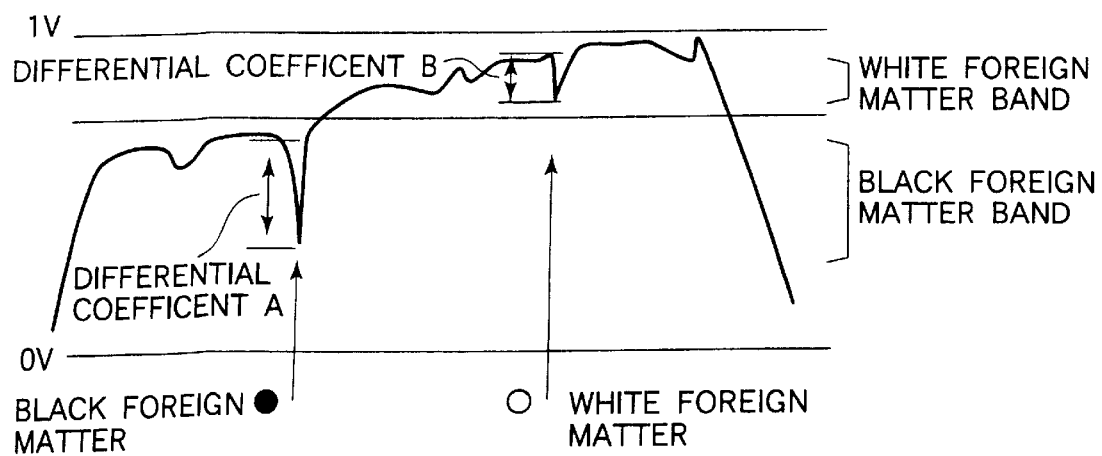
FIG. 17 is a second schematic view illustrating processing in the fourth step.

In each of the inspection devices an analog picture signal from the respective camera 11 is inputted to an image-processing part, and signal levels obtained by intensifying parts of the picture signal where the level changes sharply are compared with a reference level. After that, by scanning being carried out n times at a maximum speed, foreign matter and noise are differentiated so that foreign matter only can be detected. Also, as shown in FIG. 17, two differential slices (a white foreign matter band and a black foreign matter band) are applied simultaneously to detect foreign matter of two types, black-type and white-type, simultaneously with two different brightness levels, whereby it is possible to detect many kinds of foreign matter from fragments of plastic to hairs.

By the flat light 11Cb being brought close to (or into contact with) the flat side of the soft bag 1, diffused reflection caused by twisting or damage of the soft bag (damage arising in carriage on a conveyor of the production line) can be avoided. And as a result of the printed side of the soft bag being made the side facing the flat light 11Cb, the printing becomes dim and can be distinguished from foreign matter. Also, if a hard glass filter comprising an optical filter for preventing diffused reflection by absorbing light which is incident at an angle is used as the table 11Ca, the printing is dimmed still more by the affect of air inside the bag and the action of the filter, and foreign matter can be detected with high precision. This table 11Ca made of a hard glass filter can also be applied with the same effect to the tables 11Ca used in other steps.

[Step 5]

Figure 18:
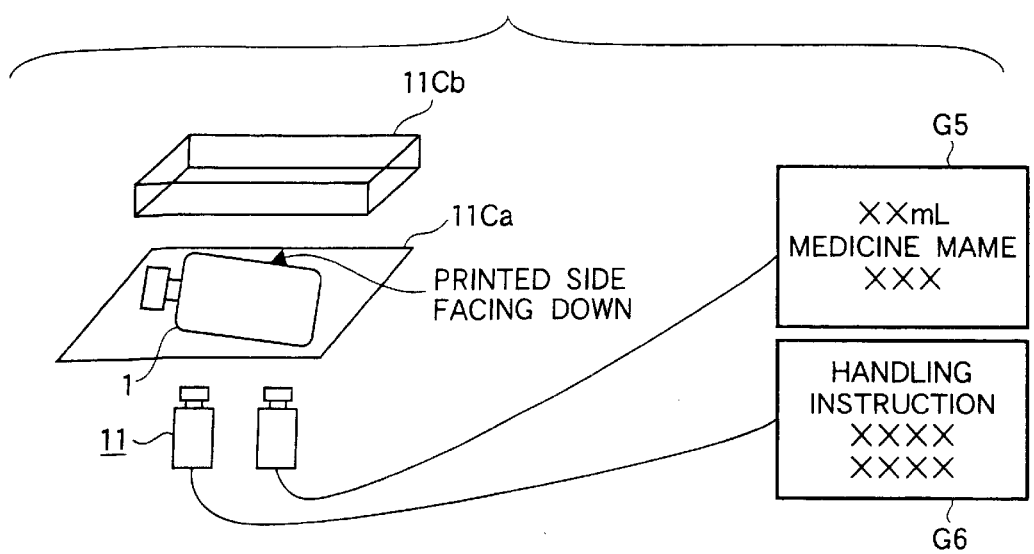
FIG. 18 is a second schematic view illustrating processing in the fifth step.

Information is printed on one side face (the front side face) of the soft bag, and as printed content for example product information such as the volume of the contents and the name and the ingredients of the medicine are printed on the approximate half-face away from the neck part, explanatory information such as cautions relating to handling are printed on the approximate half-face nearer the neck part, and markings indicating a scale of solution capacity are printed at both sides of the face. This printed content is pre-printed at the time of manufacture of the soft bag (case), and the printing does not readily become thin in heating steps; however, blurring of the printed letters sometimes occurs as the soft bag is carried on belt conveyors of the production line. In step 5, the printed side of the soft bag is shot with cameras to detect blurring (and positional deviation) of the printed letters and the inclusion of different sort of products. This detection processing will now be described with reference to FIG. 18.

In step 5, the respective robot 20 of step 5 places the soft bag 1 on the table 11Ca so that a flat face of the soft bag 1 is positioned on the upper face of the table 11Ca and the printed face of the soft bag 1 is down (facing the cameras 11), and the flat light 11Cb is brought close to or into contact with the flat side of the soft bag 1 (and thus close to the face of the glass plate 11Ca). With the soft bag 1 in this state, the flat light 11Cb shines a uniform light toward the glass plate 11Ca from above and the two cameras 11 mounted below the glass plate 11Ca pick up the light transmitted through the soft bag 1 and the table 11Ca and take an image G5 of the product information on the soft bag 1 and an image G6 of the explanatory information. These images G5 and G6 are then compared with respective master images of a good unit of product. The master images are pre-registered as inspection objects, and because in the case of a different sort of product the difference is large, for example a total of signal level differences at the pixel level is compared with a threshold value for different sort of product determination to detect a different sort of product. And for blurring of printing, similarly a sum of signal level differences at the pixel level is compared with a threshold value for print-blurring determination to check whether or not the printed letters are within a readable range (clarity of letters). Positional deviations within the printed content can also be detected by the same inspection method. Soft bags 1 passing these inspections are carried to the specified position of the following step 6.

[Step 6]

Figure 19:
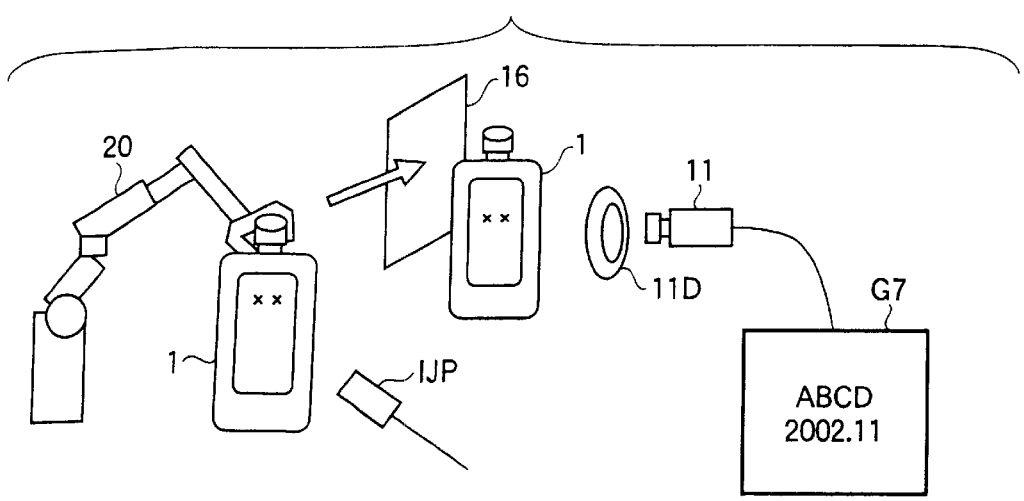
FIG. 19 is a second schematic view illustrating processing in the seventh step.

As shown in FIG. 19, for step 6, while the soft bag 1 is carried in an upright attitude by the robot 20 of step 5, printing is carried out with an IJP (Ink Jet Printer) immediately before the printing inspection step 7. The printing region is preset in correspondence with the type of the soft bag, and normally is provided between the product information and the explanatory information. With respect to the soft bag in an upright attitude with the neck part uppermost, printed information such as the date of manufacture and the serial number is printed upside down.

[Step 7]

As shown in FIG. 19, for step 7, the soft bag is carried upright to immediately in front of an optical filter 16 for preventing diffused reflection by the robot 20 of step 6, and an image G7 of the serial number and date printed by the IJP in step 5 is taken by a camera 11 from the side and compared with a master image (sum of signal levels at pixel level) of good letters to check whether or not the printed letters are within a readable range (clarity of letters). In this preferred embodiment, soft bags passing this printing check of step 7 are carried out through the exit part of the inspection stage 110 as products having passed the inspection process.

Some examples of defective units of product detected by actually operating a system according to the present invention will now be discussed.

Figure 20:
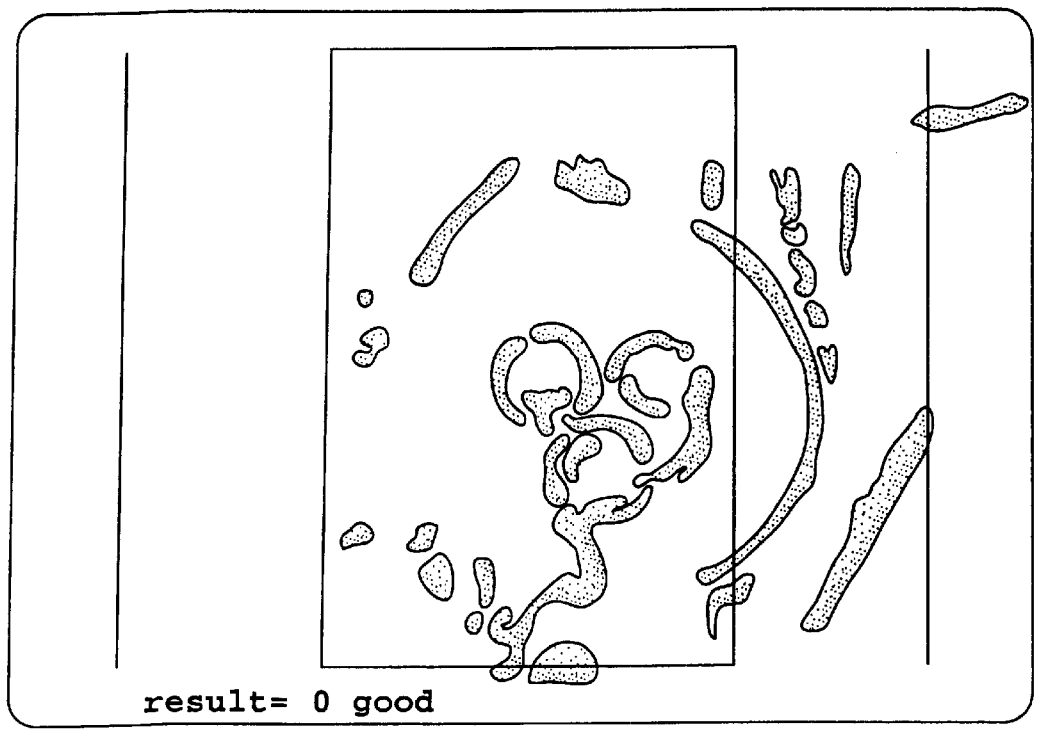
FIG. 20 is a first example of an image of a defective product detected by operating a system according to the invention.
Figure 21:
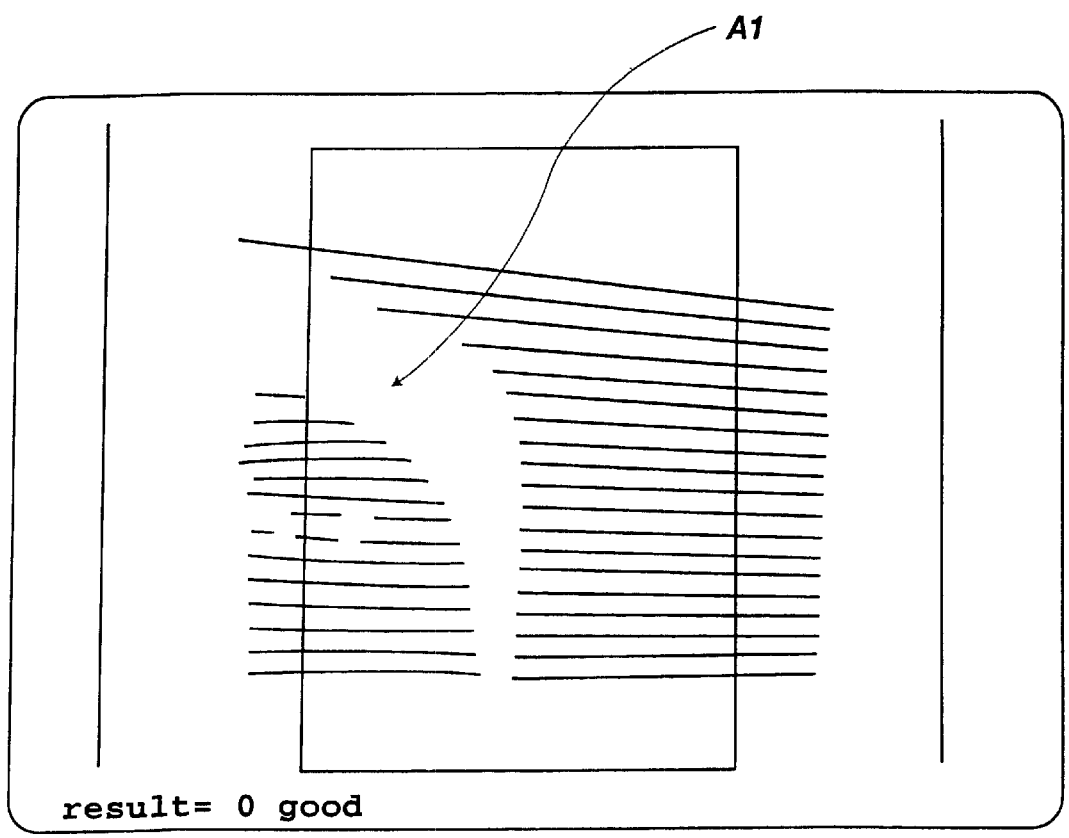
FIG. 21 is a second example of an image of a defective product detected by operating a system according to the invention.

FIGS. 20 through 23 show examples of monitor images obtained when defective samples of a soft bag for intravenous feed use were inspected and rejected by a system according to the invention. FIG. 20 shows an image of seal peeling at the top face part of the soft bag. Because where the seal is the reflectivity is high, the ring part around the three holes appears white; however, when the seal peels, this part becomes black. In the seal peeling check of step 2, this sort of difference is the basis of the determination of whether the soft bag passes or fails. FIG. 21 shows an example of an image of a shape defect caused by seal peeling. Here, the part A1 is the part where the seal has peeled. It can be seen from this that when the soft bag is checked using laser beams in the form of a grid, differences between good and defective units of product show up clearly.

Figure 22A:
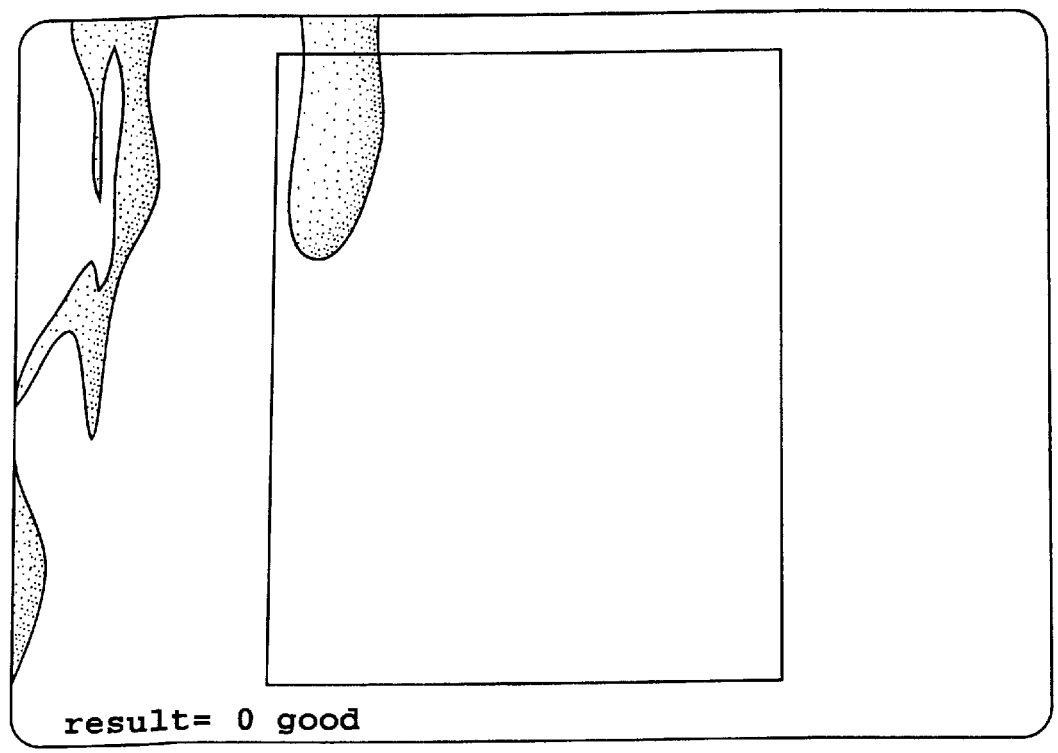
FIGS. 22A and 22B are third examples of an image of a defective product detected by operating a system according to the invention.
Figure 22B:
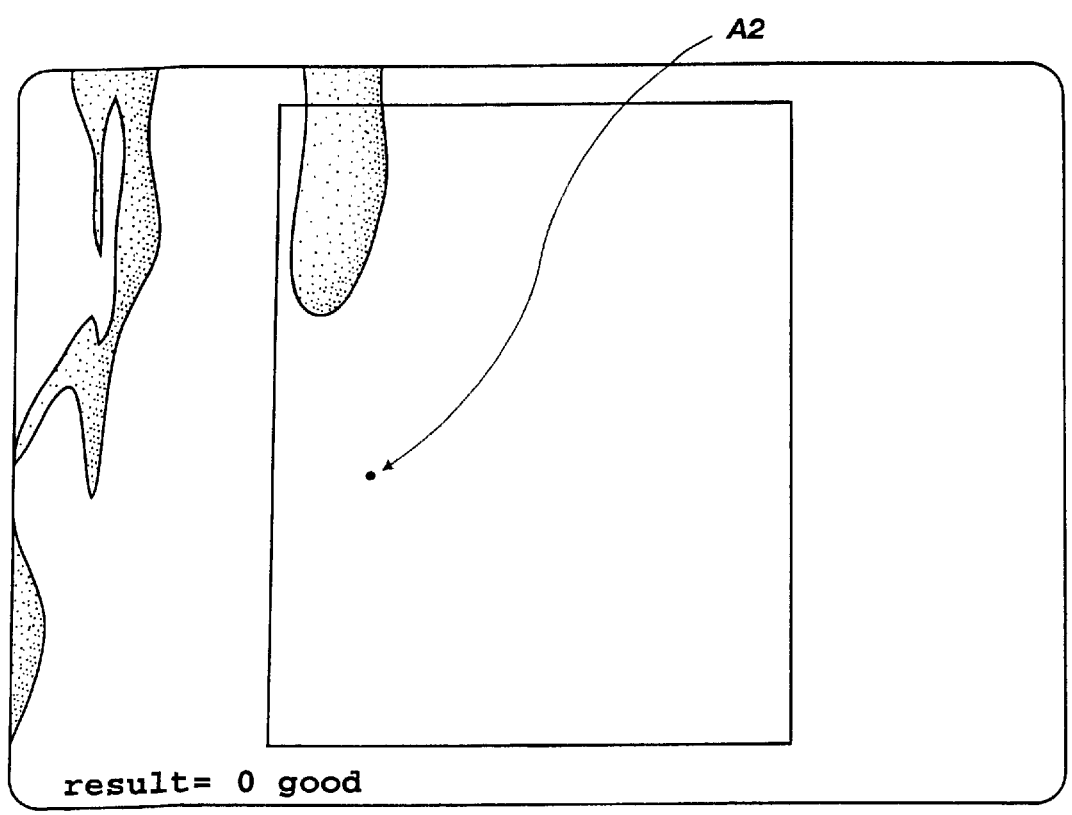
Figure 23A:
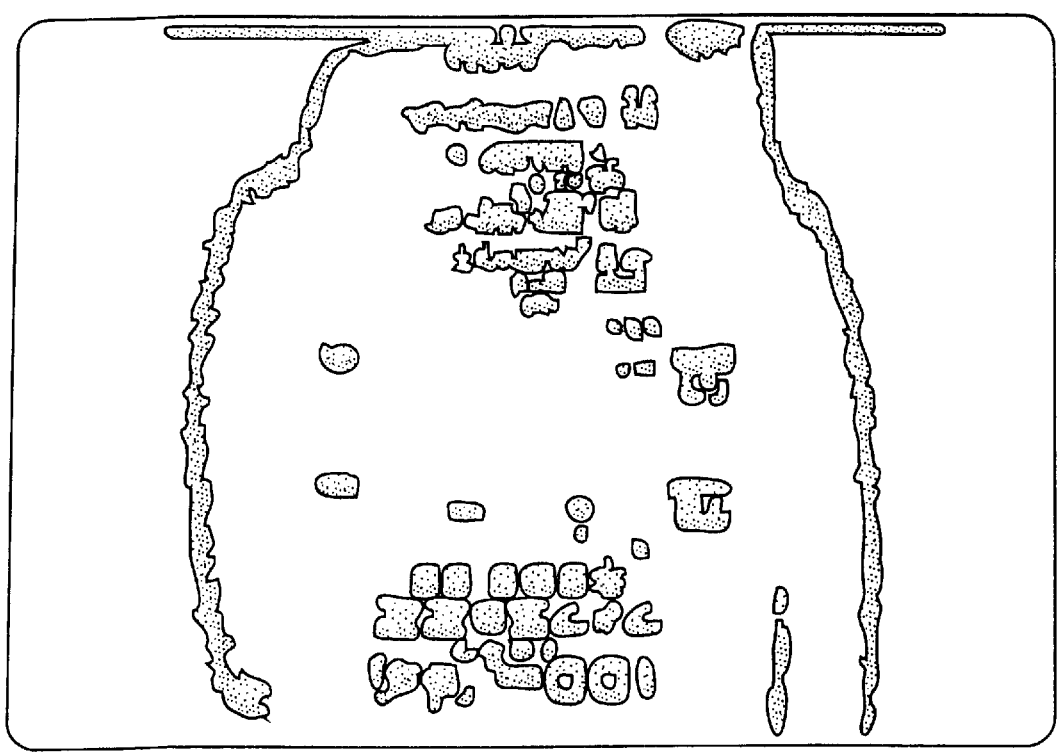
FIGS. 23A and 23B are fourth examples of an image of a defective product detected by operating a system according to the invention.
Figure 23B:
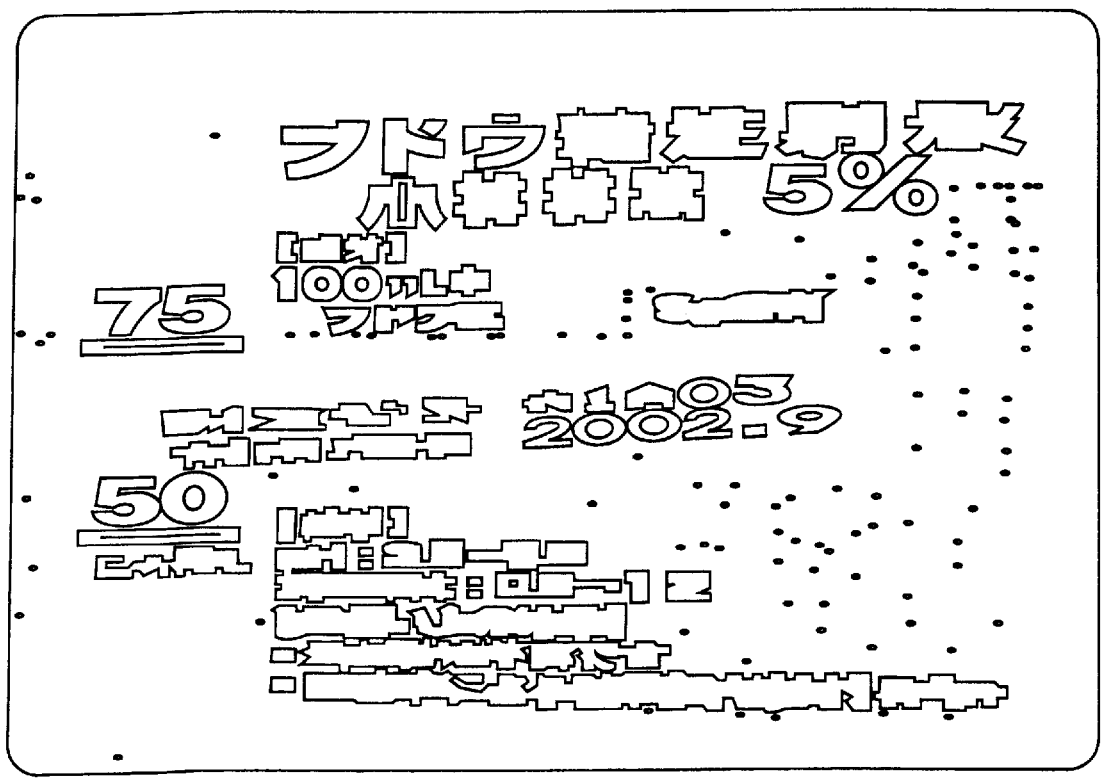

FIGS. 22A and 22B show an example of an image of a soft bag into which a takara tick has become included as foreign matter, FIG. 22A showing the raw image and FIG. 22B showing a processed image (the image after image-processing). The part A2 in FIG. 22B is the foreign matter (the takara tick), and it can be seen from FIG. 22A that a minute foreign body like this cannot be discovered by inspection with the naked eye. And although no examples will be shown here, transparent plastic fragments, hair and white foreign bodies are also difficult to detect by visual examination. FIGS. 23A and 23B show an example of an image of a soft bag on which the printing has blurred and become thin, FIG. 23A showing the image taken of the soft bag and FIG. 23B showing a master image. With this inspection system, print-blurring and defective printing can be detected with high precision by inspection on the basis of a sum of differences in signal levels at the pixel level.

Although in the preferred embodiment described above the invention was described taking a soft bag for intravenous feed use as an example, the invention can be appropriately applied to any container made of a soft material which will not readily stand on its own.

As described above, with the present invention it is possible to overcome the difficulty of inspection associated with the unstable shape peculiar to the soft bag and to carry out inspection of soft bags automatically and with high precision. Also, because time loss arising after a soft bag is carried to a destination position by a robot arm turning, that is, time lost while the arm returns to its original position, can be covered by a robot in another line, rapid carrying of soft bags becomes possible. And because laser beams are used to form an image in the form of a mesh and inspection is carried out by detecting disruption of this image, shape defects and the like can be detected with high precision. And because a step of printing information that must be printed on the soft bag on the production line is provided before a final step in the inspection process, this printed information becoming thin as a result of a heating step can be eliminated.

What is claimed is:

1. An integrated soft bag inspection system for inspecting in real time every one of soft bags arriving continuously from a production line having been filled with a liquid on the production line, using robots each having at least a robot band as carrying means for carrying the soft bags, comprising:

image pickup means for picking up all image of a soft bag;

grip position detecting means for detecting a position on a neck part of the soft bag to be gripped by the robot hand of a robot on the basis of image information from the image pickup means;

first inspection means for, on the basis of image information from the image pickup means picked up with the soft bag gripped by the neck part and held upright by a robot hand, performing a seal peeling inspection of a top face part of the soft bag and a dirt inspection of a port part;

second inspection means for, on the basis of image information from the image pickup means picked up with laser beams in the form of a mesh being radiated over an entire face of the soft bag, inspecting for shapes defects including sealing defects of the soft bag proper by detecting disruption of a mesh-form image;

third inspection means for, on the basis of image information from the image pickup means picked up with the soft bag placed lying on its side on a table made from a transparent material, inspecting for foreign matter including foreign matter included in the soft bag;

fourth inspection means for, on the basis of image information from the image pickup means picked up with the soft bag placed lying on its side on a table made from a transparent material, inspecting for blurring of printed information preprinted on the soft bag and inspecting for whether a different sort of bag is included;

printing means for printing on the soft bag while the soft bag is being carried by a robot in a vertical attitude information which must be printed on the soft bag on the production line; and fifth inspection means for inspecting the printed information printed by the printing means.

2. An integrated soft bag inspection system according to claim 1, further comprising:

a table made from a transparent material, said soft bag being placed lying on a side thereof on said table; and a flat light positioned for shining a substantially uniform light toward the underside of said table, wherein the grip position detecting means detects the position to be gripped on the neck part on the basis of an image information of the soft bag picked up by the image pickup means from above the table.

3. An integrated soft bag inspection system according to claim 2, wherein the table is made of a hard glass filter comprising an optical filter for preventing diffused reflection.

4. An integrated soft bag inspection system according to claim 1, further comprising a carrying system made up of a plurality of such robots and further comprising carrying control means for controlling the robots so that the robot hand of each robot grips the neck part of the soft bag and carries the soft bag to a predetermined inspection position and the soft bag is transferred between adjacent robots and various inspections are carried out on the soft bag successively.

5. An integrated soft bag inspection system according to claim 4, wherein the soft bag is a bag for intravenous feed use filled with au intravenous feed solution and the inspections include a foreign matter inspection and at least one inspection from among the group consisting of a seal peeling inspection of a top face part of the soft bag, a dirt inspection of a port part of the soft bag, a shape defect inspection, a print-blurring inspection and inspection for a different sort of product.

6. An integrated soft bag inspection system according to claim 1, wherein a plurality of such robots are disposed on a soft bag inspection stage in two lines facing each other and soft bags arriving in a single line from a production line are carried distributed between the robots of the two lines.

7. An integrated soft bag inspection system according to claim 6, wherein of soft bags arriving continuously in a single line from the production line soft bags in odd positions in the line are carried by one of the lines of robots and soft bags in even positions are carried by the other line of robots.

8. An integrated soft bag inspection system according to claim 1, wherein an optical filter is provided between the soft bag and the image pickup means.

9. An integrated soft bag inspection system according to claim 1, wherein the third inspection means performs the inspection for foreign matter on the basis of image information from the image pickup means picked up with the soft bag placed on the table so that a printed side of the soft bag is uppermost and with the flat light brought close to or into contact with a flat face of the soft bag.

10. An integrated soft bag inspection system according to claim 1 wherein the fourth inspection means performs the inspection for blurring of the printed information and for whether a different sort of bag is included on the basis of image information from the image pickup means picked up with the soft bag placed on the table so that a printed side of the soft bag is lowermost and with the flat light brought close to or into contact with a flat face of the soft bag.

11. An integrated soft bag inspection system for inspecting in real time every one of soft bags arriving continuously from a production line having been filled with a liquid on the production line, using robots each having at least a robot hand as a carrying structure for carrying the soft bags, comprising:

an image pickup device for picking up an image of a soft bag;

an grip position detecting device for detecting a position on a neck past of the soft bag to be gripped by the robot hand of a robot on the basis of image information from the image pickup device;

a first inspection device for, on the basis of image information from the image pickup device picked up with the soft bag gripped by the neck part and held upright by a robot hand, performing a seal peeling inspection of a top face part of the soft bag and a dirt inspection of a port pat;

a second inspection device for, on the basis of image information from the image pickup device picked up with lager beams in the form of a mesh being radiated over an entire face of the soft bag, inspecting for shape defects including sealing defects of the soft bag proper by detecting disruption of a mesh-form image;

a third inspection device for, on the basis of image information from the image pickup device picked up with the soft bag placed lying on its side on a table made from a transparent material, inspecting for foreign matter including foreign matter included in the soft bag;

a fourth inspection device for, on the basis of image information from the image pickup device picked up with the soft bag placed lying on its side on a table made from a transparent material, inspecting for blurring of printed information preprinted on the soft bag and inspecting for whether a different sort or bag is included;

a printing device for printing on the soft bag while the soft bag is being carried by it robot in a vertical attitude information which must be printed on the soft bag on the production line; and a fifth inspection device for inspecting the printed information printed by the printing device.

* * * * *